US006428666B1

(12) United States Patent
Singh et al.

(10) Patent No.: US 6,428,666 B1
(45) Date of Patent: Aug. 6, 2002

(54) ELECTROKINETIC CONCENTRATION OF CHARGED MOLECULES

(75) Inventors: Anup K. Singh, Berkeley; David W. Neyer, Castro Valley; Joseph S. Schoeniger, Oakland; Michael G. Garguilo, Livermore, all of CA (US)

(73) Assignee: Sandia National Laboratories, Livermore, CA (US)

( * ) Notice: Subject to any disclaimer, the term of this patent is extended or adjusted under 35 U.S.C. 154(b) by 0 days.

(21) Appl. No.: 09/256,586

(22) Filed: Feb. 22, 1999

(51) Int. Cl.⁷ .................. G01N 27/26; B01D 17/06
(52) U.S. Cl. ............... 204/450; 204/451; 204/518; 204/540; 204/542; 204/554; 204/600; 204/624; 204/601; 210/748
(58) Field of Search ............... 210/748; 204/450, 204/518, 520, 523, 524, 527, 535, 540, 542, 543, 544, 554, 456, 600, 606, 627, 632, 633, 634, 637, 647, 660, 451, 455, 46, 601, 605

(56) References Cited

U.S. PATENT DOCUMENTS

| | | | | |
|---|---|---|---|---|
| 3,855,130 A | * | 12/1974 | Randau et al. | 210/198.2 |
| 3,969,218 A | * | 7/1976 | Scott | 204/613 |
| 4,323,439 A | | 4/1982 | O'Farrell | 204/180 |
| 4,350,590 A | * | 9/1982 | Robinson | 204/661 |
| 4,617,102 A | | 10/1986 | Tomblin et al. | 204/299 |
| 5,116,471 A | | 5/1992 | Chien et al. | 204/180.1 |

(List continued on next page.)

FOREIGN PATENT DOCUMENTS

| | | | | |
|---|---|---|---|---|
| DE | 2305812 | A | * | 8/1974 |
| JP | 61256256 | A | * | 11/1986 |
| WO | 8911648 | | * | 11/1986 |

OTHER PUBLICATIONS

JPAB abstract of Tsuda (JP 61256256 A), Nov. 1986.*
Derwent abstract of Sonokawa (JP 07284616 A), Oct. 1995.*
JPAB abstract of Yamamura (JP359123584A), Jul. 1984.*
Derwent abstract of Nees (DE 2305812A0, Aug. 1974.*
CAPLUS abstract of Ohasi et al. ("The use of ethyl acetate for simultaneous determination of organic pesticides in water by solid–phase extraction", Jpn. J. Toxicol. Environ. Health, Tokyo (1994), 40(3), 292–7).
Richard et al. ("Solid phase versus solvent extraction of pesticides from water", Mikrochim. Acta (1986), 1(5–6), 387–94).
Junk et al. ("Interferences in solid–phase extraction using C–18 bonded porous silica cartidges", Anal. Chem. (1988), 60(13) 1347–50).
Stanley et al. ("Importance of the Accuracy of Experimental Data in the Nonlinear Chromatographic Determination of Adsorption Energy Distributions", Langmuir (1994), 10(11), 4278–85).

(List continued on next page.)

*Primary Examiner*—T. Tung
*Assistant Examiner*—Alex Noguerola
(74) *Attorney, Agent, or Firm*—Donald A. Nissen

(57) ABSTRACT

A method for separating and concentrating charged species from uncharged or neutral species regardless of size differential. The method uses reversible electric field induced retention of charged species, that can include molecules and molecular aggregates such as dimers, polymers, multimers, colloids, micelles, and liposomes, in volumes and on surfaces of porous materials. The retained charged species are subsequently quantitatively removed from the porous material by a pressure driven flow that passes through the retention volume and is independent of direction thus, a multi-directional flow field is not required. Uncharged species pass through the system unimpeded thus effecting a complete separation of charged and uncharged species and making possible concentration factors greater than 1000-fold.

14 Claims, 3 Drawing Sheets

U.S. PATENT DOCUMENTS

| | | | | |
|---|---|---|---|---|
| 5,318,680 A | * | 6/1994 | Fishman et al. | 204/180.1 |
| 5,340,452 A | | 8/1994 | Brenner et al. | 204/180 |
| 5,376,279 A | * | 12/1994 | Judd et al. | 204/518 |
| 5,405,782 A | | 4/1995 | Kohn et al. | 436/161 |
| 5,423,966 A | | 6/1995 | Wiktorowicz | 204/182.8 |
| 5,453,382 A | * | 9/1995 | Novotny et al. | 204/542 |
| 5,766,435 A | | 6/1998 | Liao et al. | 204/451 |
| 5,800,692 A | | 9/1998 | Naylor et al. | 204/601 |
| 5,863,708 A | * | 1/1999 | Zanzucchi et al. | 430/320 |

OTHER PUBLICATIONS

English language translation of Nees DE 2305812.*

Cole and Cabezas, "Recent Progress in the Electrochromatography of Proteins", *Applied Biochemistry and Biotechnology*, 54, 159–172, 1995.

Hunter, An Isotachophoresis Modle of Counteracting Chromatographic Electrophoresis (CACE), *Separation Science & Tech*. 23, 913–930, 1988.

Basak and Ladisch, "Mechanistic Description & Experimental Studies of Electrochromatography of Proteins", *AIChE J*., 41, 2499–2507, 1995.

Rudge et al., "Solute Retention in Electrochromatography by Electrically Induced Sorption", *AIChE J*., 39, 797–808, 1993.

* cited by examiner

US 6,428,666 B1

ELECTROKINETIC CONCENTRATION OF CHARGED MOLECULES

STATEMENT OF GOVERNMENT INTEREST

This invention was made with Government support under contract no. DE-AC04-94AL85000 awarded by the U. S. Department of Energy to Sandia Corporation. The Government has certain rights in the invention.

CROSS-REFERENCE TO RELATED APPLICATIONS

Not applicable.

BACKGROUND OF THE INVENTION

The present invention pertains generally to method and apparatus for separating and concentrating charged species from a carrier fluid and particularly to the use of a porous stationary phase that operates to reversibly remove and retain all the charged species, that can include molecules and particles, from a solution when a voltage gradient is applied to the porous stationary phase.

It is frequently the case that it is desired to analyze molecular species that are present in very low concentration either because the sample itself is very small or dilute or because the species of interest is present as a consequence of prior chemical processing and is thus at very low concentration. Moreover, these molecular species can be charged and being in the presence of uncharged molecules present further difficulty in analysis or separation.

For some time biochemists have exploited techniques wherein macromolecules are electrophoretically deposited onto porous membranes, such as nitrocellulose or porous glass. These membranes are generally impermeable to the macromolecular species and thus, this technique is essentially a form of ultrafiltration. Macromolecular species can also be concentrated by deposition on membranes by hydrostatic or centrifugal force. This same technique can be used for preconcentration of species prior to injection into a microfluidic analysis system. However, the species must be subsequently removed from the membrane prior to injection into an analysis column. Removal typically can be accomplished by the use of fluid flowing parallel to the surface of the membrane. In any case, removal by these methods can cause dilution of the species of interest, essentially negating at least part of the step of concentration.

There are numerous art-recognized techniques for concentration and separation of molecules that overcome the problems discussed above. Typical of these methods are those disclosed in U.S. Pat. No. 5,423,966 entitled "On Line Ion Contaminant Removal Apparatus and Method for Capillary Electrophoresis" issued to Wiktorowicz on Jun. 13, 1995 and U.S. Pat. No. 4,617,102 entitled "Process and Apparatus for Purifying and Concentrating DNA from Crude Mixtures Containing DNA" issued to Tomblin et al. Oct. 14, 1986. Here, filtration devices are used to concentrate analytes by passing a sample through a porous material. Analyte molecules smaller than the pores go through the porous structure and molecules larger than the pores are retained either within or at the upstream end of the porous material. The retained molecules can be recovered in concentrated form by reversing flow direction of the solvent or other fluid. Devices of this type retain all molecules of the size retained on the porous structure whether or not they are charged. Further, the size of the pores determine the size of the molecule trapped. If the molecule of interest is smaller than the pore size of the porous structure it cannot be retained. Thus, these methods of concentrating molecules depend upon having available a porous material that has pores of the size necessary to trap molecules of interest. Further, these methods are unable to distinguish between charged and uncharged analyte molecules.

U.S. Pat. No. 5,800,692 entitled "Preseparation Processor for Use in Capillary Electrophoresis" issued to Naylor et al. Sep. 1, 1998; U.S. Pat. No. 5,340,452 entitled "On-Column Preconcentration of Samples in Capillary Electrophoresis" issued to Brenner et al. Aug. 23, 1994; and U.S. Pat. No. 5,453,382 entitled "Electrochromatographic Preconcentration Method" issued to Novotny et al. Sep. 26, 1995 disclose another common method for concentrating an analyte, the use of a material that selectively adsorbs or binds analyte molecules allowing everything else to pass through. The adsorbed analyte can be subsequently desorbed by changing the composition of the buffer or, by way of example, by the use of electro-osmotic flow, wherein a voltage is impressed across the adsorbant to induce electro-osmotic flow thereby removing the adsorbed material from the adsorbant. Here, concentration of the analyte depends upon the selective adsorption properties of the adsorbant material consequently, these techniques generally require application-specific use of absorbent material and are unable to readily distinguish between charged or uncharged molecules. Further, desorption generally requires a change in the mobile phase or buffer.

Sample preconcentration techniques employing isotachophoresis and field-amplification in discontinuous buffer systems are disclosed in U.S. Pat. No. 5,116,471 entitled "System and Method for Improving Sample Concentration in Capillary Electrophoresis" issued to Chien et al. May 26, 1992 and U.S. Pat. No. 5,766,435 entitled "Concentration of Biological Samples on a Microliter Scale and Analysis by Capillary Electrophoresis" issued to Liao et al. Jun. 16, 1998. Isotachophoresis effects preconcentration of a sample by introducing a sample plug between two separate buffer systems and applying an electric field thereto. The leading electrolyte is chosen so that its mobility is faster than that of the ions in the sample while the mobility of the following electrolyte is slower. When an electric field is applied the ions order themselves according to their mobility causing the sample to be separated into zones containing its various ionic constituents. However, several problems have been encountered in the application of the method of isotachophoresis. In the absence of spacer ions, the different separated zones of a mixture border on each other and are thus difficult to recover without contamination from adjacent components. Spacer ions must possess very particular properties and thus are not always available. Moreover, to obtain adequate separation the components must be caused to move a considerable distance which demands a high voltage. Further, isotachophoresis has a limited capacity.

In field amplification schemes (commonly referred to as "stacking") sample ions are introduced into a capillary column in a plug of buffer solution having a significantly lower conductivity than a background buffer electrolyte. When a voltage is applied across the capillary column the region of decreased conductivity associated with the sample experiences an increase in field strength relative to that of the background electrolyte. The increased field strength causes the charged molecules of the sample to quickly migrate to the boundary of the low conductivity zone. Crossing the boundary into the region of higher conductivity (and lower field strength) causes the charged molecules of the sample to slow down which has the effect of "stacking"

the ions in the sample into a concentrated zone at the boundary of the two buffer regions. In order to be effective as a means of concentrating charged molecules, the method of field amplification requires precise control of both the conductivity of the background electrolyte as well as that of the sample. Thus, this method of sample concentration requires the use of two different and carefully tailored electrolytes; a common background electrolyte cannot be used.

Another method of concentrating the constituents of a sample is found in U.S. Pate. No. 4,323,439 entitled "Method and Apparatus for Dynamic Equilibrium Electrophoresis" issued to O'Farrell on Apr. 6, 1982 wherein a mixture of different molecular species can be concentrated by the method of electrophoresis in the presence of a counterflowing carrier fluid in a separation chamber having a particle bed with longitudinally varying separation characteristics contained therein. This technique combines size exclusion chromatography in a packed bed of particles having a gradient of exclusion limit with countervailing electrophoresis that tends to drive the molecular species in the sample in a direction opposite that imposed by fluid flow through the chromatographic column. In this way a molecule of interest is concentrated in a zone where its convective velocity is counteracted by its electrophoretic velocity; different molecular species becoming concentrated at different locations in the column. While this method of separation and concentration of molecular species is efficient it suffers from the fact that practice requires that the column be packed with materials that provide a plurality of exclusion limits plus the need for complex flow arrangements.

Prior art provides a plurality of methods for concentrating molecular species from solution. However, there are numerous problems associated with these prior methods, such as the need for specialized column packing, the need for specialized solvents or buffer solutions, the need to change solvents or buffer solutions in order to elute concentrated molecular species, the need to change flow direction or flow conditions between the steps of retaining and eluting species, and the inability to either separate charged and uncharged molecular species or effect an efficient separation. There exists therefore, a need for a simple way to effectively separate charged from uncharged molecules and concentrate the charged molecules from a dilute solution prior to analysis or other process steps.

SUMMARY OF THE INVENTION

The present invention discloses novel apparatus and method for controllably and quantitatively retaining and releasing charged species, including molecules and molecular aggregates such as dimers, polymers, multimers, colloids, micelles, and liposomes, contained in solution. The charged species are retained on a porous material, that can comprise the stationary phase in a column or flow channel, by applying a voltage gradient along the porous stationary phase in contact with the solution. The voltage gradient can cause the solution to move through the column by electroosmotic flow and can effect retention of charged species on the porous stationary phase while the solution is being passed through. The retained charged species can be subsequently completely removed from the porous stationary phase by applying a pressure differential to the column, preferably in the substantial absence of the applied voltage gradient. Thus, the present invention provides for separating charged molecules from uncharged or neutral molecules, irrespective of the size or shape difference, and for concentrating charged molecules from dilute solution using reversible electric field induced retention of charged molecules in volumes and on surfaces of porous materials. In the inventive method, uncharged molecules pass through the system unimpeded thus effecting a complete separation of charged and uncharged molecules and making possible concentration factors as least as great as 1000-fold. Moreover, the pressure driven flow that removes the retained charged molecules from the porous matrix is independent of direction and thus neither means to reverse fluid flow nor a multi-directional flow field is required-a single flow through bed can be employed in contrast to prior art systems.

DETAILED DESCRIPTION OF THE INVENTION

Figure 1A:
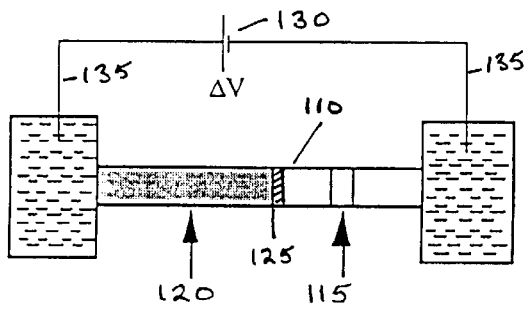
FIG. 1a and 1b illustrate an embodiment of the invention.

Before providing a detailed description of a preferred embodiment of the present invention, it should be noted that the principle upon which the present invention is based is the discovery of reversible electric field-induced retention, or trapping, of charged species, including molecules and molecular aggregates such as dimers, polymers, multimers, colloids, micelles, and liposomes, from solution in and/or on volumes and surfaces of porous materials and the subsequent removal of all or substantially all of the retained charged species by pressure driven flows that pass through the volume of porous material. By introducing a liquid sample that can contain both charged and uncharged species, such as molecules, onto a column that holds a porous stationary phase, that can be either particulate or continuous, applying a voltage to the column and its contents, along the column axis, the charged molecules can be retained on the porous stationary phase. By subsequently applying a pressure differential to the column to elute the retained charged molecules, it has been found possible to separate a wide range of charged molecules from a mixture of charged and uncharged molecules under a wide range of conditions. Moreover, the inventors have shown that charged molecules can be removed even from successive injections of solutions containing charged molecules, by the method disclosed herein. The relative volumes of the stationary phase and the sample solution to be passed through the stationary phase can vary widely and are not critical.

By providing for controlled manipulation of charged species the present invention forms the basis for applications such as, but not limited to, Concentration of dilute charged molecules up to at least 1000-fold.

Selective extraction of charged molecules from solution.

Separation of charged molecules from uncharged molecules of similar size and shape.

Control of injection volume, rate and concentration of a solution into subsequent separation and/or analysis systems.

Repeated re-concentration of molecules as they pass through various stages of systems that might cause undesirable dilution.

Chemical modification of trapped molecules by neutral reagents that are electro-osmotically transported through the porous trapping material.

Chemical modification of trapped molecules by charged reagents that are also entrapped in the porous trapping material.

Selective chemical modification of trapped molecules by reagents or catalysts that form part of the structure of the porous trapping material.

Chemical modification of neutral molecules by trapped charged molecules.

The inventive method can be summarized by two steps:

1) Application of an axial voltage differential to a solution in contact with column packed with a porous stationary phase. The solution can contain both charged and uncharged species and the species can be molecules or molecular aggregates such as dimers, polymers, multimers, colloids, micelles, and liposomes. In this step, the solution move through the column under the influence of electrophoretic and/or electro-osmotic forces. Neutral or uncharged species completely traverse the length of the column while charged species, that can be smaller or bigger than the neutral species, are retained on the stationary phase. It should be noted that retention or trapping of charged species only occurs in the presence of a porous stationary phase and while an electric field is applied along the solution flow path. The porous stationary phase can be capable of supporting electro-osmotic flow and dielectric materials such as silica, titania, alumina, zirconia and other ceramic materials and organic polymeric materials are preferred. However, dielectric materials useful as a stationary phase for this invention can take a number of other forms in addition to the more conventional materials, such as those listed above. Other preferred porous stationary phase materials can be fabricated, by way of example, by lithographic patterning and etching, direct injection molding, in-situ polymerization, sol-gel processes, high energy lithography combined with electroforming and molding (LIGA), and hot or cold embossing. Silica particles having a diameter of about 1.5 to 20 $\mu$m and containing pores having a diameter of about 50 to 500 Å are preferred as a stationary phase material and silica particles having a diameter of about 5 $\mu$m and containing pores having a diameter of about 300 Å are particularly preferred. This phenomenon of retention or trapping of charged molecules under the influence of an electric field occurs neither in an open capillary or channel nor in a capillary or channel packed with a nonporous stationary phase such as nonporous silica or polymer particles having a diameter of 1 $\mu$m or larger.

2) A pressure differential is applied to the packed column causing the charged species retained on the porous stationary phase to be eluted. While it is preferred that the pressure differential be applied in the substantial absence of an electric field, it has been found that by adjusting the relationship between applied pressure and voltage such that the pressure-driven flow is significantly greater than the electric field induced transport, the charged species can be eluted from the porous stationary phase while a voltage is being applied to the column. Further, the pressure driven flow that removes the retained charged molecules from the porous matrix is independent of direction and thus neither means to reverse fluid flow nor a multi-directional flow field is required-a single flow through bed can be employed in contrast to prior art systems.

The principle of the present invention will now be illustrated by reference to a preferred embodiment which is incorporated into and forms part of this invention. This embodiment only serves to illustrate the invention and are not intended to be limiting. Modifications and changes may become apparent to those skilled in the art, however, it is intended that the invention be limited only by the scope and content of the claims.

Figure 2A:
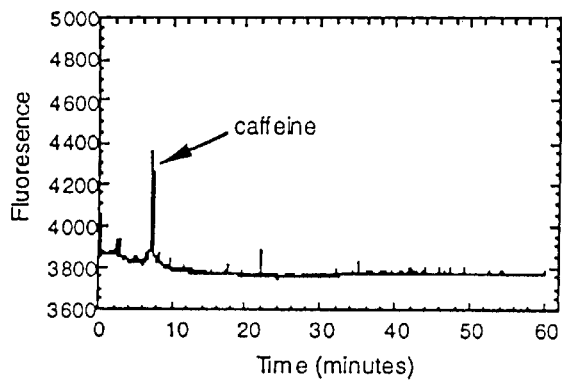
FIGS. 2a and 2b show elution curves for uncharged (2a) and charged (2b) species.
Figure 1B:
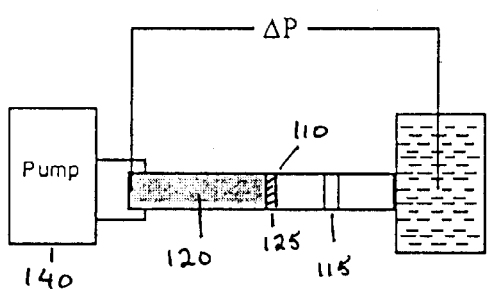
Figure 2B:
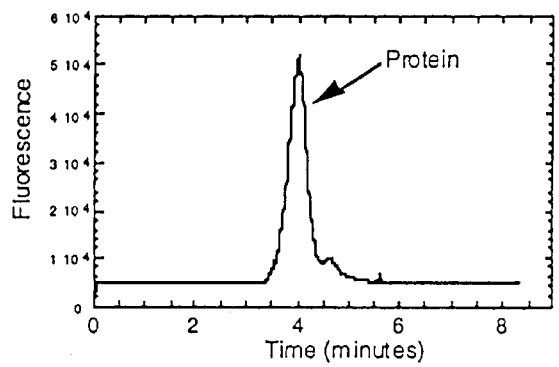

Referring now to FIG. 1a, a fused silica capillary column 110 having an internal diameter of about 100 $\mu$m was packed through at least a portion of its length with a stationary phase 120 that can consist of silica particles having a diameter of about 5 $\mu$m and pores of about 300 Å in diameter. About 10 cm of the 30 cm long column was packed with stationary phase 120 which was held in place by frits 125 or other retention means necessary to maintain the integrity of the stationary phase. The capillary column was conditioned by perfusion with 50 mM tris-hydroxymethylaminomethane (TRIS) buffer at a pH of about 8.3, although other suitable buffer materials can be used. This step was accomplished using a syringe, however, any other means of applying a pressure differential to the stationary phase can also be used. Additionally, electroosmotic flow can be used for the conditioning step. A sample containing 0.1 mg/ml of chicken egg albumin which is negatively charged protein at this pH was labeled with fluorescein to permit positive identification and detection by laser induced dispersed fluorescence, and caffeine, a neutral molecule, in 50 mM TRIS, was electrokinetically injected onto stationary phase 120 by applying a voltage of about 50 kV through the stationary phase by means of power supply 130 and electrodes 135. The electrodes are disposed on either side of stationary phase 120 and preferably in inlet reservoir 136 and outlet reservoir 137. Voltage was applied for about 10 min. at which time the uncharged caffeine was eluted from the column. Progress of this experiment was followed by addition of a detection window 115 downstream from the porous stationary phase, such as that shown in FIG. 1a, and the presence of caffeine and the labeled protein detected by laser induced dispersed fluorescence of the eluted molecules as they passed the detection window. Referring now to FIG. 2a, it can be seen that under the influence of the applied electric field only neutral caffeine was eluted in about 8 minutes from packed column 110. There was no evidence that the negatively charged chicken egg albumin was eluted from the column even though voltage was maintained on the column for over 60 minutes. In similar experiments, voltage could be maintained for as long as 12 hours without any evidence of elution of chicken egg albumin. In identical capillaries packed with 5 $\mu$m nonporous silica particles and in open capillaries, chicken egg albumin would elute in less than 20 minutes under the influence of applied voltage. When it was evident nothing more would elute from column 110, application of voltage was stopped and pressure is applied to the inlet end of column 110 by pressure means (FIG. 1b), such as a pump 140 or other means designed to force fluid through the column, thereby eluting those charged molecules that have been retained on stationary phase 120, FIG. 2b.

Figure 3:
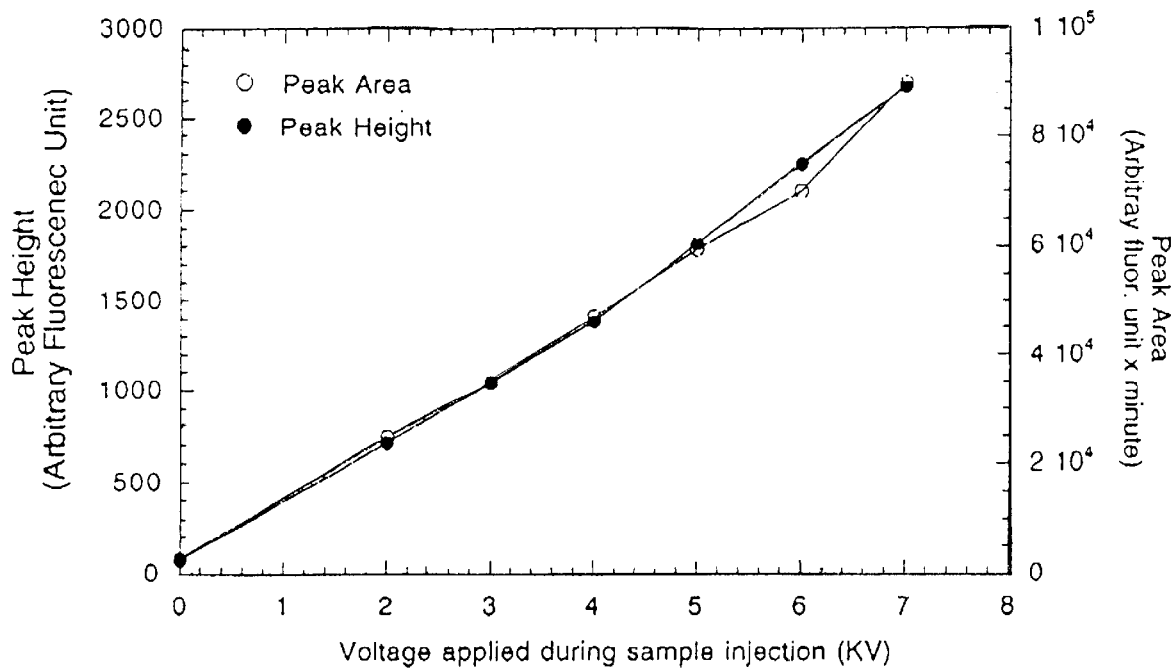
FIGS. 3–5 show recovery of injected analyte as a function of the quantity injected onto an analysis column.
Figure 4:
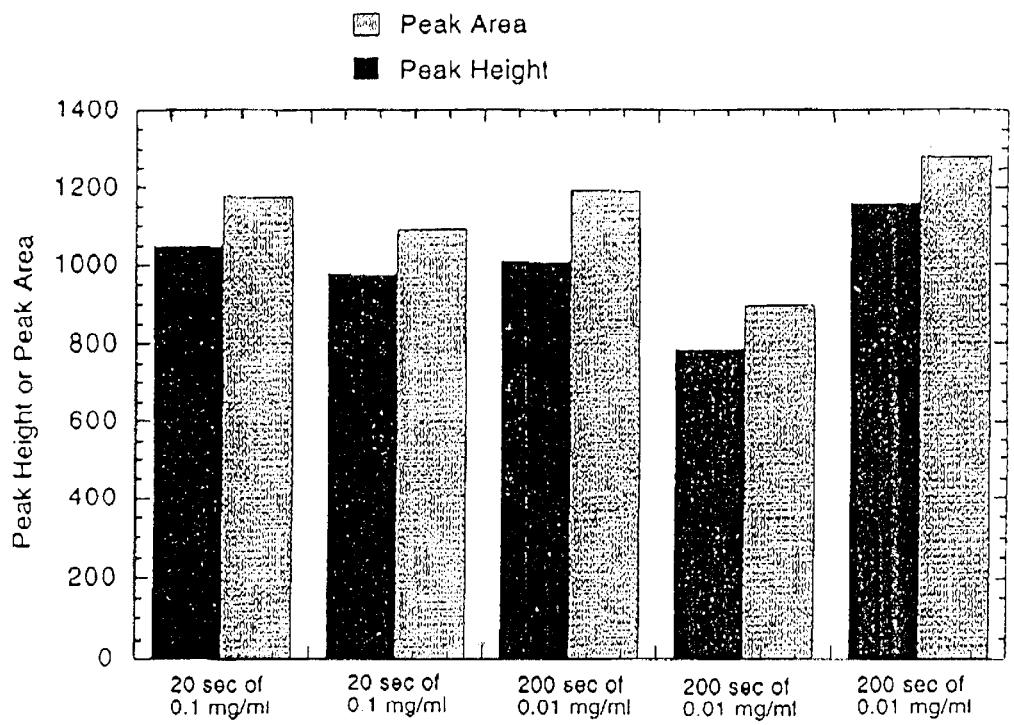
Figure 5:
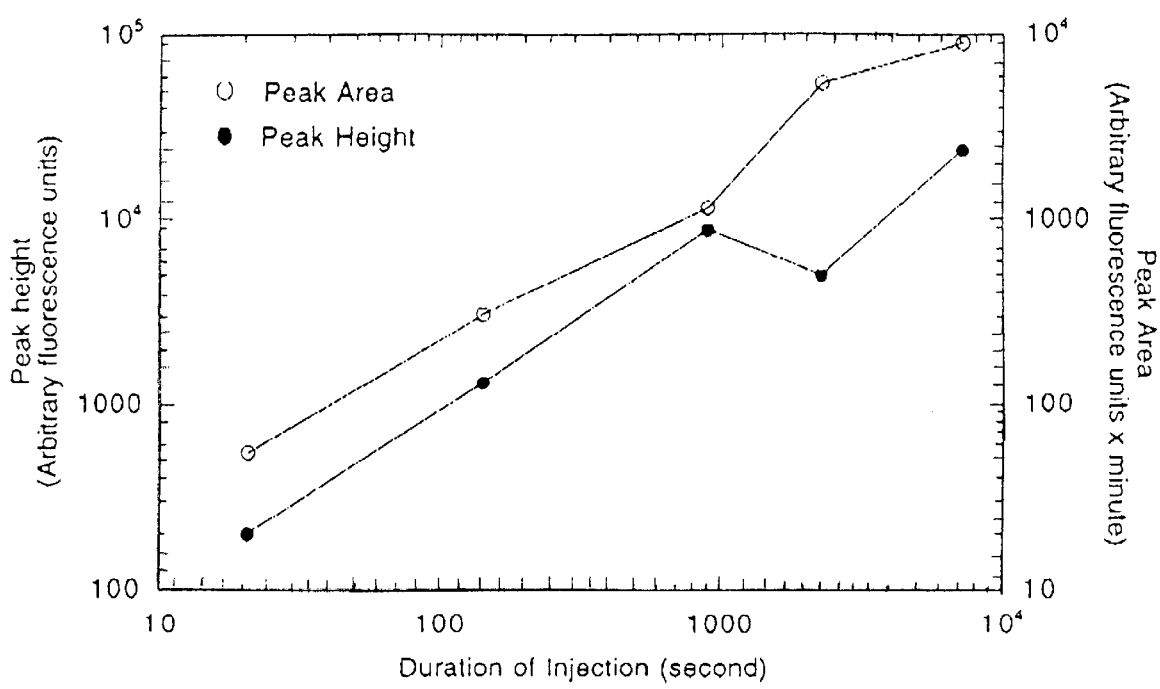

That the porous stationary phase retains and releases all or substantially all of the charged molecular material deposited thereon under the influence of an applied electric field is illustrated by FIGS. 3–5. Referring now to FIG. 3, here various quantities of a solution containing 0.1 mg/mL of chicken egg albumin were injected into column packed with porous silica. The quantity of chicken egg albumin injected was determined by the injection voltage (the injection time was held constant at 20 sec.). Following the injection period, the sample was caused to flow through the stationary phase by applying an electric potential of 5 kV along the column. Subsequently, the chicken egg albumin was eluted from the column by applying a hydrostatic pressure of about 2000 psi to the column. It can be seen that there was a linear relationship, as measured by both the peak height and area, between the amount of chicken egg albumin injected and recovered. It should be further noted that the relationship between peak height and area remains constant regardless of the amount of chicken egg albumin present on the column.

FIG. 4 shows the effect of concentration of analyte in a sample on the amount recovered. Here, the product of analyte concentration in the sample and injection time was maintained constant, i.e., the quantity of analyte injected onto the porous stationary phase was constant. As before, the sample was caused to flow through the stationary phase by applying an electric potential of 5 kV along the column and the analyte retained on the porous stationary phase was eluted by application of about 2000 psi hydrostatic pressure. It can be seen that, within reasonable experimental error, the amount of analyte recovered from the column was constant even though the concentration of analyte in the sample varied by a factor of about ten.

FIG. 5 shows an alternative mode of presenting the data shown in FIG. 3. Here, different amounts of analyte are injected onto the stationary phase (porous silica) by varying the duration of the injection time at a constant injection voltage of 5 kV. The analyte retained on the porous stationary phase, following electroosmotic flow of the sample through the column, was eluted from the stationary phase by application of about 2000 psi hydrostatic pressure.

Further, FIGS. 3 and 5 demonstrate the manner in which the inventive method can be used to concentrate charged molecules. This can be done by either increasing the voltage during sample injection (FIG. 3) or the time of sample injection (FIG. 5) for a constant injection voltage. For a given quantity of charged analyte in a sample, concentration of the charged analyte can be achieved by injecting a large quantity of the sample onto a column, either injecting the sample for a longer period of time or at a higher voltage and then eluting the charged analyte retained on the porous stationary phase. Since the peak height, which is a measure of the quantity of charged analyte eluted from the porous stationary phase, increased with the amount of sample injected in a given volume of solution the quantity of charged analyte eluted from the column had increased, i.e., the analyte had been concentrated.

In summary, the present invention discloses and describes a method for quantitatively and controllably retaining and removing charged species, including molecules and molecular aggregates such as dimers, polymers, multimers, colloids, micelles, and liposomes, from a solution by reversible electric field-induced retention of charged species in volumes and surface of porous materials and apparatus for same. By providing a porous material having a size and porosity that, in the presence of an electric field, and particularly in the presence of electric field-induced flow, will trap, retain, and subsequently release all the charged species under the influence of pressure-driven flow, the present inventive method provides means for the controlled manipulation of molecules and thus, the means to separate charged from uncharged molecules, concentrate charged molecules from dilute solution, and chemically modify molecules regardless of differences in size and shape between the charged and uncharged molecules.

The foregoing is intended to be illustrative of the present invention and are not to be construed as a limitation or restriction thereon, the invention being delineated in the following claims.

We claim:

1. A method of controllably retaining and releasing charged species contained in solution, comprising:
   a) passing the solution through a porous stationary phase disposed in a column by imposing a voltage gradient between first and second ends of the column; and
   b) subsequently subjecting the column to a pressure gradient between first and second ends of the column, wherein the porous stationary phase is comprised of a porous dielectric material.

2. The method of claim 1, wherein the steps of passing and subjecting are in opposite directions.

3. The method of claim 1, wherein the porous stationary phase is a porous particulate dielectric material.

4. The method of claim 3, wherein the porous particulate material has a diameter of less than about 7 $\mu$m and contains pores having a diameter of less than about 500 Å.

5. The method of claim 4, wherein the porous particulate material has a diameter of about 5 $\mu$m and contains pores having a diameter of about 300 Å.

6. The method of claim 3, wherein the porous particulate material is selected from the group consisting of ceramic and organic polymeric materials.

7. The method of claim 6, wherein the ceramic material includes porous silica.

8. The method of claim 1, wherein the porous stationary phase is fabricated by methods including packing porous particles into the column, lithographic patterning and etching, direct injection molding, sol-gel processing, in-situ polymerization, and high energy lithography combined with electroforming and molding (LIGA), and hot embossing or cold embossing.

9. The method of claim 1, wherein the porous stationary phase is a continuous phase.

10. A method for treating a solution to separate charged species from uncharged species contained therein, comprising:
    a) passing the solution through a porous stationary phase disposed in a column by imposing a voltage gradient along the column, wherein the porous stationary phase is a porous dielectric material; and
    b) subsequently subjecting the column to a pressure differential.

11. The method of claim 10, further including concentrating the separated charged species.

12. A microfluidic device for controllably retaining and releasing charged species contained in a solution, comprising:
    a) a solid substrate fabricated to define a microchannel disposed thereon, the microchannel having a fluid inlet and outlet;
    b) spaced electrodes in communication with said microchannel;
    c) a porous stationary phase disposed in said microchannel, wherein said porous stationary phase is comprised of a porous dielectric material;
    d) means for applying a pressure gradient to the microchannel to remove retained charged particles; and
    e) means for applying an electric potential to said spaced electrodes.

13. A method for chemically modifying charged molecules and molecular aggregates, comprising:
    a) retaining charged molecules and molecular aggregates on a porous dielectric material by passing a solution containing the charged molecules and molecular aggregates through a porous stationary phase dispersed in a column by imposing a voltage gradient along the column, wherein the porous stationary phase is comprised of the porous dielectric material and is particulate or continuous;

b) flowing a solution containing reagent molecules past the retained charged molecules and molecular aggregates; and c) subsequently subjecting the column to a pressure differential to cause chemically modified charged molecules and molecular aggregates retained on the porous stationary phase to be eluted therefrom.

14. The method of claim 13, wherein the step of flowing includes electroosmotic flow.

* * * * *